US006441036B1

(12) United States Patent
Berge

(10) Patent No.: US 6,441,036 B1
(45) Date of Patent: Aug. 27, 2002

(54) FATTY ANALOGUES FOR THE TREATMENT OF OBESITY, HYPERTENSION AND FATTY LIVER

(75) Inventor: Rolf Berge, Bønes (NO)

(73) Assignee: Thia Medica AS, Bergen (NO)

( * ) Notice: Subject to any disclaimer, the term of this patent is extended or adjusted under 35 U.S.C. 154(b) by 0 days.

(21) Appl. No.: 09/700,061

(22) PCT Filed: Apr. 23, 1999

(86) PCT No.: PCT/NO99/00135

§ 371 (c)(1),
(2), (4) Date: Jan. 27, 2001

(87) PCT Pub. No.: WO99/58121

PCT Pub. Date: Nov. 18, 1999

(30) Foreign Application Priority Data

May 8, 1998 (WO) .............................. PCT/NO98/00143

(51) Int. Cl.$^7$ .............................................. A01N 37/02
(52) U.S. Cl. .......................... 514/552; 514/550; 554/77; 554/85; 554/88; 554/218; 560/147; 560/149; 560/155; 560/179; 562/899
(58) Field of Search ............................... 554/77, 85, 88, 554/213; 560/147, 149, 155, 179; 514/550, 552; 562/899

(56) References Cited

FOREIGN PATENT DOCUMENTS

| EP | 345038 | * 11/1993 |
| EP | 0843972 | 5/1998 |
| WO | 97/03663 | * 2/1997 |

OTHER PUBLICATIONS

Forman et al. (1997), "Hypolipidemic Drugs, Polyunsaturated Fatty Acids, and Eicosanoids Are Ligands For Peroxisome Proliferator–Activated Receptors α and δ," *Proc. Natl. Acad. Sci. USA* 94:4312–4317.

* cited by examiner

*Primary Examiner*—Deborah D. Carr
(74) *Attorney, Agent, or Firm*—Reed & Associates

(57) ABSTRACT

The present invention relates to novel fatty acid analogous of the general forumla I: $CH_3-[CH_2]_m-[x_i-CH_2]_n-COOR$, as defined in the specification, which can be used for the treatment and/or prevention of obesity, fatty liver and hypertension. Further, the invention relates to a nutritional composition comprising such fatty acid analogues, and a method for reducing the total weight, or the amount of adipose tissue in an animal. The invention also relates to a method for improving the quality of product such as meat, milk and eggs.

68 Claims, 8 Drawing Sheets

FATTY ANALOGUES FOR THE TREATMENT OF OBESITY, HYPERTENSION AND FATTY LIVER

This application is a 371 of PCT/NO99/00135 filed Apr. 23, 1999.

The present invention relates to novel fatty acid analogous which can be used for the treatment and/or prevention of obesity, fatty liver and hypertension. Further, the invention relates to a nutritional composition comprising such fatty acid analogues, and a method for reducing the total weight, or the amount of adipose tissue in an animal. The invention also relates to a method for improving the quality of product such as meat, milk and eggs.

BACKGROUND OF THE INVENTION

Hyperlipidemia and obesity afflict an increasing proportion of the population in Western societies and are associated with the development of serious conditions such as atherosclerosis, hypertension, fatty liver and insulin resistance. These conditions may eventually lead to the clinical manifestations of coronary heart diseases (CD) and non-insulin dependent diabetes mellitus (NIDDM).

Treatment with modified fatty acids represent a new way to treat these diseases.

EP 345.038 describes the use of non-β-oxidizable fatty acid analogues for the treatment of hyperlipidaemic conditions and for reducing the concentration of cholesterol and triglycerides in the blood of mammals.

PCT/NO95/00195 describes alkyl-S—CH$_2$COOR and alkyl-Se—CH$_2$COOR for the inhibition of the oxidative modification OF ldl.

It has now been found that the analogues described in the prior art publication mentioned above, i.e. non-β-oxidizable fatty acids substituted with Sulphur or Selenium in the 3-position have broader area of applications.

Further, we have now synthesized and characterized novel fatty acid analogues which impose an effect on obesity, hypertension and fatty liver.

In feeding experiments with the fatty acid analogues in accordance with the present invention, the results show that these compounds lower the adipose tissue mass and body weight, and are thus potent drugs for the treatment of obesity and overweight.

Further, we have shown that the fatty acid analogues are potent antidiabetic compounds, with a profound effect on the levels of glucose and insulin.

Further, the compounds have been proved to have an favourable effect on restenosis, and exhibit good anti-oxidative properties.

Obesity

Obesity is a chronic disease that is highly prevalent in modern society and is associated not only with a social stigma, but also with decreased life span and numerous medical problems, including adverse psychological development, reproductive disorders such as polycystic ovarian disease, dermatological disorders such as infections, varicose veins, Acanthosis nigricans, and eczema, exercise intolerance, diabetes mellitus, insulin resistance, hypertension, hypercholesterolemia, cholelithiasis, osteoarthritis, orthopedic injury, thromboembolic disease, cancer, and coronary heart disease.

Existing therapies for obesity include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery. Caloric restriction as a treatment for obesity causes catabolism of body protein stores and produces negative nitrogen balance.

Considering the high prevalence of obesity in our society and the serious consequences associated therewith as discussed above, any therapeutic drug potentially useful in reducing weight of obese persons could have a profound beneficial effect on their health. There is a need in the art for a drug that will reduce total body weight of obese subjects toward their ideal body weight without significant adverse side effects, and which also will help the obese subject to maintain the reduced weight level.

It is therefore an object of the present invention to provide a treatment regimen that is useful in returning the body weight of obese subjects toward a normal, ideal body weight.

It is another object to provide a therapy for obesity that results in maintenance of the lowered body weight for an extended period of time. Further, is is an object to reduce or inhibit the weight gain normally induced by fat rich diets.

It is yet another object to prevent obesity and, once treatment has begun, to arrest progression or prevent the onset of diseases that are the consequence of, or secondary to, the obesity, such as hypertension and fatty liver. These and other objects will be apparent to those of ordinary skill in the art.

The obesity herein may be due to any cause, whether genetic or environmental. Examples of disorders that may result in obesity or be the cause of obesity include overeating and bulimia, polycystic ovarian disease, craniopharyngioma, the Prader-Willi Syndrome, Frohlich's syndrome, Type II diabetics, GH-deficient subjects, normal variant short stature, Turner's syndrome, and other pathological conditions showing reduced metabolic activity.

Hypertension

Increased blood pressure is a common condition in the developed countries of the world where, in very broad terms, the population eat too much and do not take sufficient exercise. Hypertension can have a variety of uncomfortable and dangerous side effects and it is seen as a major risk factor in relation to coronary heart disease. Hypertension can be associated with specific causes such as kidney disease or adrenal tumours but in most instances it is not. Obesity is regarded as a risk factor in relation to hypertension and a first line strategy in relation to obese hypertensive patients is to suggest weight reduction. It is therefore reasonable to anticipate that the present compounds, e.g. TTA and TSA which can have an effect on obesity, will reduce hypertension.

Specific ailments attributable to hypertension include heart failure, myocardial infarction, rupture or thrombus of the blood vessels in the brain, and kidney damage.

It is therefore an object of the present invention to provide a treatment regimen that is useful in lowering the blood pressure.

Fatty liver

The mechanism of production of fatty hepatosis is not entirely clear, but appears to be a combination of several factors, such as sparing action of ethanol oxidation on utilization of liver triacylglycerols, excessive mobilization of triacylglycerols from adipose tissue to the liver caused in part by action of ethanol in triggering release of hormones, and failure to synthesize sufficient lipoprotein for transport of triacylglycerols because of alterations of amino acid availability.

Fatty cirrhosis is characterized by the liver cells being infiltrated with fat (triacylglycerols). The infiltration usually being due to alcohol ingestion.

The explanation for the ethanol induced increase in hepatic deposition of fat is still not very well understood. However, most investigators believe that ethanol inhibits hepatic fatty acid oxidation which secondarily causes fatty acids to be stored as triacylglycerol.

Fatty liver as a concomitant of the ingestion of high fat diets, alcohols or chlorinated hydrocarbons is a well-known phenomenon. Chronic intake of ethanol results in, among other things, hepatic injury to the accumulation of triglycerides and eventually, cirrhosis.

It is thus an object of the present invention to provide a treatment regimen that is useful in lowering the concentration of triacylglycerols in the liver. It is anticipated that such a regimen will provide an inhibiting effect on the development of a fatty liver condition, and also be suited as a method for the treatment of the manifested disease.

The compounds of the present invention both activates the β-oxidation, and also reduces the concentration of triglycerieds in the liver.

Mechanisms of action

Minor modifications of natural fatty acids, sulphur, selenium or oxygen replacing one or more of carbons in the fatty acid backbone. The compounds defined by the formula I have properties which give them a unique combination of biological effects.

Tetradecylthioacetic acid (TTA) is most thoroughly studied and we have shown several beneficial effects in various test animals.

The studies have shown that TTA has properties very similar to natural fatty acids, the main difference being that TTA is not oxidised by the mitochondrial β-oxidation system. However, the presence of compounds of the present invention have been shown to increase the β-oxidation of other (non-substituted fatty acids).

Administration of TTA to rats for 12 weeks nearly doubled the hepatic and plasma content of monounsaturated fatty acids (mainly oleic acid), while polyunsaturated fatty acids (mainly linoleic acid and DHA) decreased. Thus the compound of the present invention modifies the composition of the lipids in various tissues. It is also shown that the present compounds modifies the fat content, and it is anticipated that the present compounds also will modify the fat distribution.

Feeding moderate doses of TTA to animals like rats, mice, rabbits and dogs decreased both plasma cholesterol and triacylglycerol levels within days of treatment. We have also shown the same effect for TSA, and compounds of the present invention with Sulphur substituted in positions 5 or 7 have been shown to increase the β-oxidation and it is thus anticipated that also these fatty acid analogous will lower the plasma levels of triglycerides and cholesterol. TTA and TSA are far more potent in this respect than polyunsaturated fatty acids like EPA.

As mentioned above, an important mechanism of action of 3-thia fatty acids is a significant increased mitochondrial fatty acid oxidation reducing the availability of fatty acids for esterification. The synthesis of triacylglycerol and cholesterol is reduced and the secretion of VLDL from the liver is decreased (10). This has the effect of reducing the production of LDL. All these effects seem to be at least partly mediated by peroxisome proliferator activated receptors (PPAR), ubiquitous transcription factors involved in the regulation of lipid metabolism. We have shown that TTA is a potent ligand of PPARα, a transcription factor regulating the catabolism of fatty acids and eicosanoids, and a less potent ligand of PPARγ, which is involved in the regulation of adipocyte differentiation.

Obesity is a common feature of non insulin dependent diabetes mellitus (NIDDM) and a risk factor for its development. NIDDM is often linked to hypertension, dyslipidemia, elevated levels of plasma free fatty acids and an increased risk of cardiovascular disease. NIDDM patients are characterised by resistance to insulin action on glucose uptake in peripheral tissues and dysregulated insulin secretion.

We have shown that TTA decrease hyperinsulinemia and markedly improved insulin action on glucose utilisation. TTA did also prevent diet-induced insulin resistance. In contrast to the prior known antidiabetic glitazones TTA did not increase body weight gain.

These effects may at least partly be explained by increased influx of fatty acids and enhanced fatty acid oxidation in the liver. The data thus suggest a role for TTA in both lipid and glucose homeostasis in vivo.

As clearly shown in the experimental section the compounds of the present invention inhibit an increase in the body weight and adipose tissue mass of animals given either a high fat or a high sucrose diet. This make the compounds of the present invention very suitable as pharmaceutical and/or nutritional agents for the treatment of obesity, i.e. the compounds can be used as a slimming agent to provide a body weight or adipose tissue weigh reduction.

Further the compounds of the present invention can be used as an anti-diabetic drug by reducing the concentration of glucose in the blood. We have also shown that the compounds of the present invention reduce the plasma concentration of insulin in hyperinsulineamic animals. For animals which possesses a reduces sensitivity to insulin, the compounds of the present invention have been shown to strengthen the effect of endogenous insulin.

The term <<metabolic syndrome>> is used to describe a multimetabolic syndrome which is inter alia characterised by hyperinsulinemia, insulin resistance, obesity, glucose intolerance, Type 2 diabetes mellitus, dyslipidemia or hypertension.

As indicated above the compounds of the present invention have been shown to provide a positive effect on all the conditions mentioned above, i.e. by regulating both the glucose and lipid homeostasis, and thus it is anticipated that the compounds of the present invention will be suitable agents for the regulation of the above defined metabolic disease (sometimes called syndrome X).

DETAILED DESCRIPTION OF THE INVENTION

The present invention discloses that modified fatty acid analogues at non-cytotoxic concentrations can be used for the treatment and/or prevention of obesity, hypertension and fatty liver.

The present invention relates to the use of fatty acid analogues of the general formula (I):

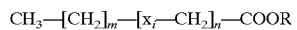

wherein n is an integer from 1 to 12, and wherein m is an integer from 0 to 23, and wherein i is an odd number and indicates the position relative to COOR, and wherein $X_i$ independent of each other are selected from the group comprising O, S, SO, $SO_2$, Se and $CH_2$, and wherein R represents hydrogen or $C_1$–$C_4$ alkyl, with the proviso that at least one of the $X_i$ is not $CH_2$, or a salt, prodrug and complex thereof, for the preparation of a pharmaceutical composition for the treatment and/or prevention of obesity.

In particular, the invention relates to the use of a compound of the general formula I wherein $m \geq 13$. That is a compound which contains at least 14 carbons on the ω side of the X group.

A presently preferred embodiment of the invention is the use of a compound of formula I wherein $X_{i=3}$ is selected from the group consisting of O, S, SO, $SO_2$ and Se, and wherein $X_{i=5-25}$ is $CH_2$.

Tetradecylthioacetic acid (TTA) and Tetradecylselenioacetic acid (TSA), i. e. $X_{i=3}$ are Sulphur and Selenium, respectively is presently preferred compounds.

Furthermore, the present invention relates to the use of a compound of the formula I for the preparation of a pharmaceutical composition for the treatment and/or prevention of hypertension.

A further aspect of the invention relates to the use of a compound of the formula I for the preparation of a pharmaceutical composition for the treatment and/or prevention of fatty liver.

Still a further aspect of the invention relates to the use a compound of the formula I for the preparation of a pharmaceutical composition for the treatment and/or prevention of the multi metabolic syndrome termed <<metabolic syndrome>> which is inter alia characterised by hyperinsulinemia, insulin resistance, obesity, glucose intolerance, Type 2 diabetes mellitus, dyslipidemia and/or hypertension.

We have also synthesised and characterised novel fatty acid analogues, and thus in accordance with the present invention there is provided novel compounds of the formula I:

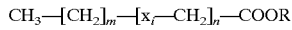
$$CH_3-[CH_2]_m-[x_i-CH_2]_n-COOR$$

wherein n is an integer from 1 to 12, and wherein m is an integer from 0 to 23, and wherein i is an odd number and indicates the position relative to COOR, and wherein $X_i$ independent of each other are selected from the group comprising O, S, SO, $SO_2$, Se and $CH_2$, and wherein R represents hydrogen or $C_1$–$C_4$ alkyl, with the proviso that at least one of the $X_i$ is not $CH_2$.

A further aspect of the invention relates to a method for the treatment or prevention of an obese or overweight condition, said method comprising the step of administering to an animal in need thereof an effective amount of fatty acid analogues of the general formula (I):

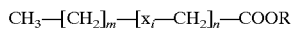
$$CH_3-[CH_2]_m-[x_i-CH_2]_n-COOR$$

wherein n is an integer from 1 to 12, and wherein m is an integer from 0 to 23, and wherein i is an odd number and indicates the position relative to COOR, and wherein $X_i$ independent of each other are selected from the group comprising O, S, SO, $SO_2$, Se and $CH_2$, and wherein R represents hydrogen or $C_1$–$C_4$ alkyl, with the proviso that at least one of the $X_i$ is not $CH_2$, or a salt, prodrug and complex thereof.

In accordance with the method indicated above, preferred embodiments are as follows:

said animal is a human.

said animal is an agricultural animal, such as gallinaceous birds, bovine, ovine, caprine or porcine mammals.

said animal is a domestic or pet animal, such as dog or cat.

said animal is a fish or shellfish, such as salmon, cod, Tilapia, clams, oysters, lobster or crabs.

The treatment involves administering to a patient in need of such treatment a therapeutically effective concentration which is maintained substantially continuously in the blood of the animal for the duration of the period of its administration.

Further, the invention relates to a pharmaceutical composition for the prevention and/or treatment of obesity, hypertension or fatty liver. Preferably, the pharmaceutical composition comprises in admixture with the fatty acid analogues a pharmaceutically acceptable carrier or excipient.

The invention also relates to a nutritional composition comprising an amount of fatty acid analogues of the general formula (I) effective to reduce, or to prevent an increase in, the total body weight or the total body fat mass in a human or non-human animal, and a method for producing weigh loss or a reduction of the fat mass in a human or non-human animal in need thereof, comprising administering thereto an effective amount of a composition comprising fatty acid analogues of the general formula (I).

Preferred embodiments relate to a conditions wherein the animal has developed an obese condition or is low energy adapted.

Still another embodiment of the invention relates to the modification of the fat distribution, concentration and content of animals in order to improve the quality of the meat, visually, nutritionally and customer acceptability or product such as milk and eggs.

Preferred embodiments include agricultural animals, such as gallinaceous birds, bovine, ovine, caprine or porcine mammals, or fish or shellfish, such as salmon, cod, Tilapia, clams, oysters, lobster or crabs.

FIGURE LEGENDS

DEFINITIONS USED IN THE APPLICATION

Obesity

Figure 1:
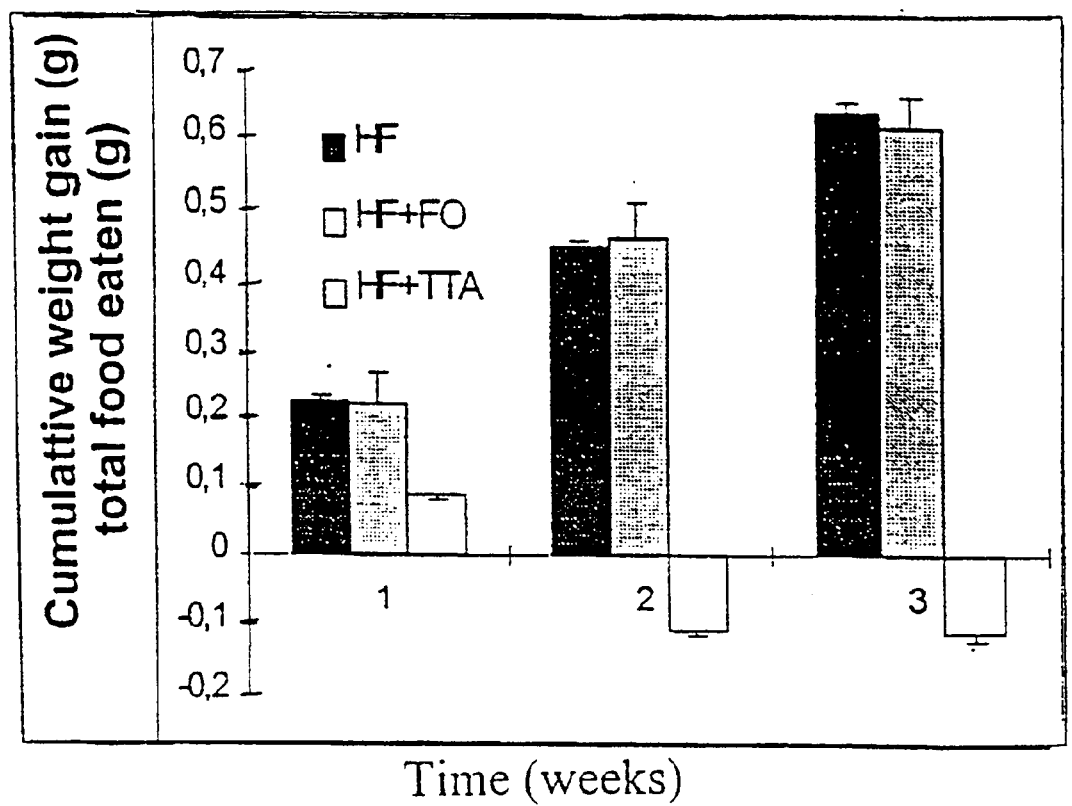
FIG. 1 shows the effect of TTA on weight gain for rats given a high fat diet.

The term <<obesity>> normally refers to a condition whereby an animal has a Body Mass Index (BMI) which is above 25,9. However, in this specification and the accompanying claims, the term <<obesity>> has a broader interpretation, i.e. indicating a condition wherein the BMI is above a desired value (above normal and below BMI). The term obesity also covers the medical definition <<simple obesity>> which is a condition resulting when the caloric intake exceeds energy expenditure.

Low Energy Adapted

The term <<low energy adapted>> refers to a condition whereby an animal has a low energy consumption, i.e. less then normal.

Animals

In this context the term <<animals>> include mammals such as humans and farm (agricultural) animals, especially the animals of economic importance such as gallinaceous birds, bovine, ovine caprine and porcine mammals, especially those that produce products suitable for the human consumption, such as meat, eggs and milk, such as. Further, the term is intended to include fish and shellfish, such as salmon, cod, Tilapia, clams and oysters. The term also includes domestic animals such as dogs and cats.

Treatment

In relation to obesity, the term <<treatment>> refers to a reduction of the severity of the disease, e.g. by reducing the total body weight or by reducing the fat mass.

Prevention

In relation to obesity, the term <<prevention>> refers to preventing obesity from occurring, i.e. a compound of the present invention is administered prior to the onset of the obese condition. This means that the compounds of the present invention can be used as prophylactic agents to inhibit weight gain, or to impede an increase in body fat mass.

ADMINISTRATION OF THE COMPOUNDS OF THE PRESENT INVENTION

As a pharmaceutical medicament the compounds of the present invention may be administered directly to the animal by any suitable technique, including parenterally, intranasally, orally, or by absorption through the skin. They can be administered locally or systemically. The specific route of administration of each agent will depend, e.g., on the medical history of the animal.

Examples of parenteral administration include subcutaneous, intramuscular, intravenous, intraarterial, and intraperitoneal administration As a general proposition, the total pharmaceutically effective amount of each of the compounds administered parenterally per dose will preferably be in the range of about 5 mg/kg/day to 1000 mg/kg/day of patient body weight, although, as noted above, this will be subject to a great deal of therapeutic discretion. For TTA it is expected that a dose of 100–500 mg/kg/day is preferable, and for TSA the dosage could probably in the range of from 10 to 100 mg/kg/day.

If given continuously, the compounds of the present invention are each typically administered by 1–4 injections per day or by continuous subcutaneous infusions, for example, using a mini-pump. An intravenous bag solution may also be employed. The key factor in selecting an appropriate dose is the result obtained, as measured by decreases in total body weight or ratio of fat to lean mass, or by other criteria for measuring control or prevention of obesity or prevention of obesity-related conditions, as are deemed appropriate by the practitioner.

For parenteral administration, in one embodiment, the compounds of the present invention are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the compounds of the present invention each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier may suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or non-ionic surfactants such as polysorbates, poloxamers, or PEG.

For oral pharmacological compositions such carrier material as, for example, water, gelatine, gums, lactose, starches, magnesium-stearate, talc, oils, polyalkene glycol, petroleum jelly and the like may be used. Such pharmaceutical preparation may be in unit dosage form and may additionally contain other therapeutically valuable substances or conventional pharmaceutical adjuvants such as preservatives, stabilising agents, emulsifiers, buffers and the like. The pharmaceutical preparations may be in conventional liquid forms such as tablets, capsules, dragees, ampoules and the like, in conventional dosage forms, such as dry ampulles, and as suppositories and the like.

The treatment with the present compounds may occur without, or may be imposed with, a dietary restriction such as a limit in daily food or calorie intake, as is desired for the individual patient.

In addition, the compounds of the present invention are appropriately administered in combination with other treatments for combatting or preventing obesity.

The invention will be more fully understood by reference to the following examples. They should not, however, be construed as limiting the scope of the invention.

EXPERIMENTAL SECTION

Methods

Obese Zucker (fa/fa) Rats

The obese Zucker (fa/fa) rats used in this study were bred at the U 465 INSERM animal facility from pairs originally provided by the Harriet G. Bird Laboratory (Stow, Mass., USA). Unless otherwise stated, the animals were maintained under a constant light-dark cycle (light from 7:00 a.m. to 7:00 p.m.) at 21±1° C. and were given free access to food and water. Three rats were housed per cage. Weight gains were recorded daily.

Wistar Rats

Male Wistar rats Charles River rats weighing 280–358 g were purchases from AnLab Ltd. (Prague, Czech Repubic) and housed in wire-mesh cages in a temperature (22±1° C.) and light-controlled (light from 7:00 a.m. to 7.00 p.m.) room. They were given free access to chow and water. Three rats were housed per cage. Weight gain and food intake were recorded daily.

Diets (Given in Weight %) Used in the Feeding Experiments

Standard Chow Diet

Rats were fed a Standard Laboratory Rat Chow ST1 from Velaz, Prague, Czech Republic.

High Sucrose Diet (HS)

50.3% sucrose, 4.8% gelatin, 3.2% hay, 2.3% vitamins and minerals, 8.7% yeast, 8.7% dried milk, 12.3% casein, 9% beef tallow, 1% sunflower oil.

HS+TTA: Same as HS+0.3% TTA dissolved in the beef tallow.

HS+fish oil (FO): Beef tallow and sunflower oil is replaced by 10% Triomar. Triomar is from Pronova Biocare, Norway and contains 33.4% EPA, 3.1% DPA and 20.2% DHA.

High fat (HF): 1.9% gelatin, 5.7% wheat bran, 7.7% vitamins and minerals, 25.4% corn starch, 25.7% casein, 26.8% beef tallow and 7.1 % sunflower oil.

HF+TTA: Same +0.4% TTA dissolved in the beef tallow.

HF+FO: 10% beef tallow is replaced by 10% Triomar.

Intravenous Glucose Tolerance Tests

Male Zucker (fa/fa) rats (5 weeks old) were anaesthetised after a 5-hours fast, by intraperitoneal injection of sodium pentobarbital (50 mg/kg). The rats were injected with glucose (0.55 g/kg) in the saphenous vein and blood samples were collected from the tail vein in heparinized tubes at time 0, 5, 10, 15, 20 and 30 minutes after the glucose load. Samples were kept on ice, centrifuged and plasma was stored at −20° C. until analysis.

Hyperinsulinemic Euglycemic Clamp

After 21 days on their respective diets (see above), the rats were anaesthetised by injection of xylazine hydrochloride (Rometar SPOFA, Prague, Czech Republic; 10 mg/ml) and ketamine hydrochloride (Narkamon SPOFA, Prague, Czech republic; 75 mg/ml), and fitted with chronic carotid artery and jugular vein cannulas as described by Koopmans et al. (Koopmans, S. J., et al., Biochim Biophys Acta, 1115, 2130–2138 1992.). The cannulated rats were allowed to recover for two days after surgery before the clamping studies which were carried out according to Kraegen et al. (Kraegen, E. W., et al., Am J Physiol, 248, E353–E362 1983.). Thus, on the third day after surgery, unrestrained conscious rats were given a continuous infusion of porcine insulin (Actrapid, Novo Nordisk, Denmark) at a dose of 6.4 mU per kg per min to achieve plasma insulin levels in the upper physiological range. The arterial blood glucose concentration was clamped at the basal fasting level, by variable infusion of a 30% w/v glucose solution (Leciva, Prague, Czech Republic). Blood samples for determination of plasma glucose and insulin concentrations were obtained every 15 minutes from the start of the glucose infusion. After 90 minutes, the rats were disconnected from the infusions and immediately decapitated, blood was collected for plasma separation, liver and epididymal adipose tissue pads were dissected out and weighed.

Measurement of Plasma Parameters

Glucose (GLU, Boehringer Mannheim, Germany), free fatty acids (NEFA, C ACS-ACOD kit; Wako Chemicals, Dalton, USA) and b-hydroxybutyrate (310-A kit; Sigma Diagnostics Inc., St. Louis, USA) concentrations were measured using enzymatic methods. Insulin concentrations were determined with radioimmunoassay by (CIS bio International, Gif sur Yvette, France) using rat insulin as standard in the Zucker rats. In the Wistar Charles River rats, plasma glucose concentrations were measured with the aid of Beckman Glucose Analyzer (Fullerton, Calif., USA). Plasma insulin levels were measured using a RIA kit from Linco Research Inc. (St. Charles, Mo., USA). Phospholipids were measured by the enzymatic method of bioMérieux, Marcy-lEtoile, France, Triacylglycerol by the Technicon Method no. SA4-0324L90, USA and Cholesterol by the Technicon Method no. SA4-0305L90, USA.

Preparation of Post-nuclear and Mitochondrial Fractions and Measurement of Enzyme Activities Freshly isolated livers from individual old Zucker rats, were homogenised in ice-cold sucrose buffer (0.25 M sucrose, 10 mM HEPES (pH 7.4) and 2 mM EDTA). Post-nuclear and mitochondrial fractions were prepared using preparative differential centrifugation according to DeDuve et al. (De Duve, C., et al., Biochem. J., 60, 604–617 1955.) Modifications, purity and yield were as described earlier (Garras, A., et al., Biochim. Biophys. Acta, 1255, 154–160 1995.). Acid soluble products were measured in post-nuclear and mitochondrial enriched fractions, using [$1$-$^{14}$C]-palmitoyl-CoA and [$1$-$^{14}$C]-palmitoyl-L-carnitine (Radio-chemical Centre, Amersham, England) as substrates as described earlier (Willumsen, N., et al., J. Lipid Res., 34, 13–22 1993. Carnitine palmitoyltransferase-I and -II activities were measured in the post-nuclear and mitochondrial fractions essentially as described by Bremer (Bremer, J., Biochim. Biophys. Acta, 665, 628–631 1981.) and 3-hydroxy-3-methylglutharyl-CoA synthase was measured according to Clinkenbeard et al. (Clinkenbeard, K. D., et al., J. Biol. Chem, 250, 3108–3116 1975.) in the mitochondrial fractions.

RNA Analysis

RNA extraction (Chomczynski, P., et al., Anal. Biochem., 162, 156–159 1987.), Northern blot analysis and slot blotting of RNA onto nylon filters, and hybridisation to immobilised RNA were performed as earlier described (Vaagenes, H., et al., Biochem. Pharmacol., 56, 1571–1582 1998.). The following CDNA fragments were used as probes: CPT-I, (Esser, V. et al., J. Biol. Chem., 268,5817–5822 1993), CPT-II (Woeltje, K. F., et al., J. Biol. Chem., 265, 10720–10725 1990.), 3-hydroxy-3-methylglutharyl-CoA synthase (Ayté, J., et al., Proc. Natl. Acad. Sci. USA., 87, 3874–3878 1990.), and hormone sensitive lipase (Holm, C., et al., Biochim. Biophys. Acta, 1006, 193–197 1989.). The relative levels of RNA expression were estimated as the amounts of radioactive probe hybridised to the respective levels of 28S rRNA.

RESULTS

EXAMPLE 1

Preparation and Characterisation of the Compound a) Synthesis of the Novel Compounds Fatty acids with the heteroatom in variable positions were synthesized according to the general description for 3-substituted analogues (see below) with the following modification:

Alkyl-Hal was replaced by Alcanoic-Hal and HS—CHCOOR was replaced by alkyl-SH.

The following fatty acid analogous have been prepared and characterised:

| Compound | Reactants | Melting-point (° C.) |
|---|---|---|
| Dodecanylthiobutanoic acid | 4-bromobutanoic acid + dodecanylthiol | 54–55 |
| Decanylthiohexanoic acid | 6-bromohexanoic acid + decanylthiol | 50–51 |
| Octanylthiooctanoic acid | 8-bromooctanoic acid + octanylthiol | 39–40 |

Purification of products as described below. Purity >95%. Structure was verified by mass spectrometry.
b) The Synthesis of the 3-substituted Fatty Acid Analogous The compounds used according to the present invention wherein the substituent $X_{i=3}$ is a sulphur atom or selenium atom may be prepared according to the following general procedure:
X is a Sulphur Atom The thio-substituted compound used according to the present invention may be prepared by the general procedure indicated below

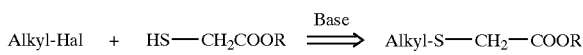

The sulphur-compound, namely, tetradecylthioaceticacid (TTA), $(CH_3-(CH_2)_{13}-S-CH_2-COOH$ was prepared as shown in EP-345.038.
X is a Selenium Atom the seleno-substituted compound used according to the present invention may be prepared by the following general procedure 1. Alkyl-Hal+KSeCN=>Alkyl-SeCN . . .
2. Alkyl-SeCN+$BH_4^-$=>Alkyl-Se$^-$
3. Alkyl-Se$^-$+$O_2$=>Alkyl-Se—Se-Alkyl This compound was purified by carefully crystallisation from ethanol or methanol.

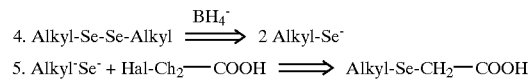

The final compound, e.g. when alkyl is tetradecyl, $(CH_3-(CH_2)_{13}-Se-CH_2-COOH$ (tetradecylselinioacetic acid (TSA)) can be purified by crystallisation from diethyl ether and hexane. This product may be fully characterised by NMR, IR and molecular weight determination.

The methods for the synthesis and isolation of these Sulphur and Selenium compounds, and the compound wherein X of formula I is Oxygen (O), Sulphur-I-oxide (SO) and Sulphurdioxide ($SO_2$) are described in European Patent No. 345.038, and International Patent Application No. WO 97/03663.

EXAMPLE 2

Toxicity Study of TTA

A 28 days toxicity study in dogs according to GLP guide-lines has been performed by Corning Hazleton (Europe), England. Oral administration of TTA at dose levels up to 500 mg/kg/day was generally well tolerated. Some lipid related parameters were lowered in the animals given high dosages. This is consistent with the pharmacological activity of TTA.

The dose level of 500 mg/kg/day also elicited body weight loss. There was no evidence of toxicity at dose levels of 50 or 500 mg/day/kg.

Tests for mutagenic activity have been performed by Covance Laboratories Limited, England. It was concluded that TTA and TSA did not induce mutations in strains of *Salmonella typhimurium* and *Escherichia coli*. Furthermore, TTA was not mutagenic when tested in mouse lymphoma cells and L5178Y.

The concentration of the compounds tested in *S. typhimurium* and *E. coli* 3–1000 mg/plate (TTA) 2–5000 mg/plate (TSA). In mouse lymphoma cells, L5178Y, the concentration was 2.5–50 mg/ml. TSA and TSA were found not to be mutagenic in these tests. TSA and TTA have been tested for chromosomal aberrations in cultured Chinese hamster ovary cells and no aberrations were induced by the doses tested (12–140 mg/ml).

The compounds of the present invention are therefore potentially useful as pharmaceutical compounds in this respect.

EXAMPLE 3

TTA Induces a Lipid Lowering Effect in Obese Animals

Male obese Zucker fa/fa rats, weighing 100 g at the start of the experiment, were housed in pairs in metal wire cages in a room maintained at 12 h light-dark cycles and a constant temperature of 20±3° C. The animals were acclimatised for at least one week under these conditions before the start of the experiment.

TTA (tetradecylthioacetic acid) prepared in accordance with procedure described previously, and palmitic acid (control), was suspended in 0.5% (w/v) carboxymethyl cellulose (CMC). Six animals were used in both groups. TTA (tetradecylthioacetic acid) and palmitic acid were administered at a dose of 300 mg/day/kg body weight, by gastric intubation (gavage) once daily for 10 days. The rats were fasted for 2 hours before termination of the experiment. Blood and organs were collected. Lipid concentrations in plasma were determined using an autoanalyzer, as described in the method section. Results obtained are reported in Table 1.

TABLE 1

| Effect of TTA on lipid levels in obese Zucker fa/fa rats. Decreased lipid level in plasma (% of control) | | | |
|---|---|---|---|
| | Triglycerides | Cholesterol | Phospholipids |
| TTA | 72 | 73 | 71 |

The results clearly demonstrates that the TTA decreases the levels of triglycerides, cholesterol and phospholipid in the plasma.

EXAMPLE 4

TTA and TSA Induce a Lipid Lowering Effect in Normal Animals (Wistar Rats)

Male Wistar rats, weighing 180–200 g at the start of the experiment, were housed individually in metal wire cages in a room maintained at 12 h light-dark cycles and a constant temperature of 20±3° C. The animals were acclimatised for one week under these conditions before the start of the experiments.

TTA, TSA and eicosapentaenoic acid (EPA) were suspended in 0.5% (w/v) carboxymethyl cellulose (CMC). Six animals were used for each treatment, and a 0.5% CMC solution was administrated to the rats as control. After administration of the test compound, the rats were fasted for 12 hours and anaesthetised with haloethan. The EPA and the fatty acid derivatives were administered by gastric intubation (gavage) once daily for 7 days. Blood samples were collected by cardiac puncture, and lipid concentrations in plasma were determined as outlined in the method section. The results are given in table 2

TABLE 2

Effect of TTA, TSA and EPA - on plasma lipid levels in rats.

| Compound | Dose mg/day/kg body weight | Plasma lipids (% reduction of control) | |
| --- | --- | --- | --- |
| | | tri-glycerides | cholesterol |
| TSA | 15 | 25 | 20 |
| EPA | 1500 | 20 | 18 |
| TTA | 150 | 45 | 30 |

Table 2 shows that TTA exhibits a good lipid lowering effect in blood of rats. It will appear that a 100 times greater dose of the EPA is necessary to obtain the same decrease in the plasma lipid concentration as obtained for TSA. Moreover, the substituted fatty acid compounds of the present invention are much more effective than pure EPA and fish oil in lowering plasma lipids. Therefore they are potentially useful as medical compounds.

EXAMPLE 5

TTA Influence on High Fat Diets Fed to Wistar Charles River Rats

Male Wistar Charles River rats (280–360 g) were fed 3 different diets (see methods) for 3 weeks ad libitum. Afterwards, they were killed by decapitation, liver and epididymal adipose tissue pads were dissected out and weighed.

Feeding the Wistar rats the high fat diet thus increased the epididymal and retroperitoneal fad pad weight. TTA treatment prevented the increase in adipose tissue mass and this effect was independent of food consumption, which was identical (high fat: 15.1±1.1 vs. high fat+TTA: 14.8±1.3 g/rat/day.

TABLE 3

Influence of high fat diets with and without TTA supplement for three weeks on body weight gain, liver weight and adipose tissue weights in high fat diet fed Wistar Charles River rats.

| Parameters | Standard chow diet | High fat diet − TTA | High fat diet + TTA |
| --- | --- | --- | --- |
| Epididymal adipose tissue (g) | 3.0 ± 0.1 | 5.3 ± 0.3 | 3.1 ± 0.2 |
| Epididymal adipose tissue/body weight (%) | 0.8 ± 0.03 | 1.3 ± 0.1 | 1.0 ± 0.1 |

TABLE 3-continued

Influence of high fat diets with and without TTA supplement for three weeks on body weight gain, liver weight and adipose tissue weights in high fat diet fed Wistar Charles River rats.

| Parameters | Standard chow diet | High fat diet − TTA | High fat diet + TTA |
| --- | --- | --- | --- |
| Retroperitoneal adipose tissue (g) | 2.2 ± 0.2 | 5.5 ± 0.3 | 2.7 ± 0.2 |
| Retroperitoneal adipose tissue/ body weight (%) | 0.6 ± 0.1 | 1.4 ± 0.1 | 0.8 ± 0.05 |

Data are given as means ± SEM.

EXAMPLE 6

TTA Decreases the Total Body Weight of Normal Rats 2 groups of 6 male Wistar Rats were randomly selected, and studied for weight development over a period of 12 week. The body weight of each Wistar rat was measured at the start of the experiment. All animals in both groups received individually the same amount of food (nutrition) during the experimental period of 12 weeks. All animals in one of the groups were orally administrated with the medicament comprising TTA. The other group was the control group (CMC). After the 12 week period the body weight of rats were measured again.

The results given in table 4 show that oral administration of TTA leads to significant weight loss.

TABLE 4

Effect of TTA on body weight of male Wistar rats after 12 weeks of treatment.

| | Body weight gain/g |
| --- | --- |
| control (rats not treated with TTA) | 294 ± 27 |
| TTA | 234 ± 20 |

EXAMPLE 7

TTA Influence on High Fat Diets Fed to Wistar Charles River Rats

FIG. 1 shows the cumulated values for weight gain (g)/total food eaten (g) over 3 weeks. The values were calculated by taking the daily average weight gain and dividing it by the average amount of food eaten that day. See method section for the abbreviations and the specification of the diets.

The composition of the diets are given in the method section.

EXAMPLE 8

TTA Influence on High Sucrose Diets Fed to Wistar Charles River Rats

Figure 2:
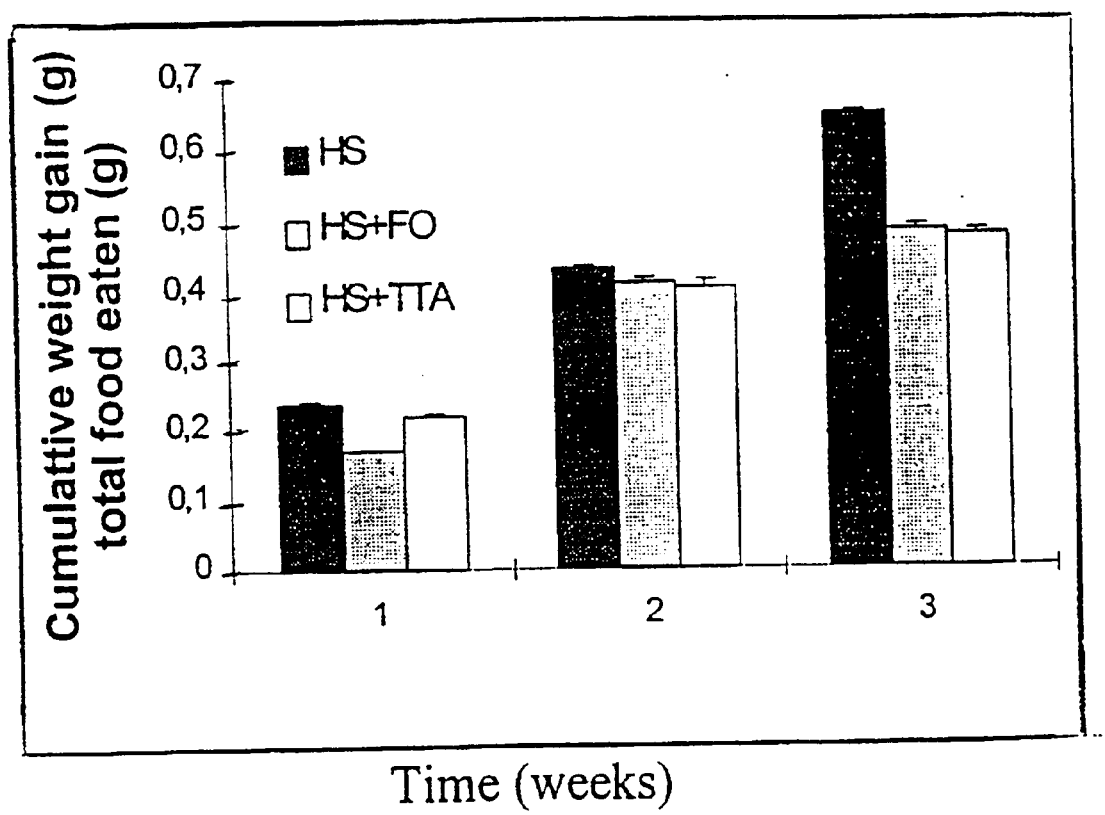
FIG. 2 shows the effect of TTA on weight gain for rats given a high sucrose diet.

FIG. 2 shows the cumulated values for weight gain (g)/total food eaten (g) over 3 weeks. The values were calculated by taking the daily average weight gain and dividing it by the average amount of food eaten that day. See method section for the abbreviations and the specification of the diets.

The composition of the diets are given in the method section.

EXAMPLE 9

Influence of TTA on Body Weight Gain, Liver and Adipose Tissue Weight in Obese Animals The TTA was also tested for its effect on liver and adipose tissue weight. The results are indicated in table 5.

5 week-old male obese Zucker (fa/fa) rats fed with TTA, 300/kg/day suspended in 0.5% CMC. Control animals received CMC only. Following 11 days of treatment, rats were killed by cervical dislocation, liver and epididymal adipose tissue pads were dissected out and weighed. Data are means±SD of 6 animals in the control- and 6 animals in the experimental group.

TABLE 5

Influence of TTA on body weight gain, liver and adipose tissue weights in young obese Zucker (fa/fa) rats.

| Parameters | Control | Treated |
|---|---|---|
| Liver weight (g) | 7.79 ± 0.26 | 10.6 ± 0.70 |
| Epididymal adipose tissue/body weight % | 0.98 ± 0.02 | 0.78 ± 0.02 |
| Body weight gain (g/day) | 5.91 ± 0.37 | 6.23 ± 0.28 |

EXAMPLE 10

TTA Induces a Weight Reduction in Dogs 3 male dogs (4–6 months old) were housed singly during the days. Each animal was offered 400g of SQC Diet A each morning after dosing and any residue diet was removed in the afternoon. The drug was administered orally in capsules once daily for 28 days.

TABLE 6

Mean body weights of male dogs treated with 500 mg/kg/day TTA for 4 weeks.

| Week | 0 | 1 | 2 | 3 | 4 |
|---|---|---|---|---|---|
| Body weight (kg) | 9.22 ± 1.77 | 8.95 ± 1.61 | 8.75 ± 1.58 | 8.58 ± 1.66 | 8.50 ± 1.74 |

EXAMPLE 11

TTA Treatment Prevents HF Diet Induces Hyperinsulinemia in Normal Rats

Rats weighing 280–360 g were divided into 3 groups (n=6) and fed with three different diets: standard rat chow, high fat diet (HF) and HF supplemented with TTA. After 21 days on their respective diets, blood was collected after an overnight fast from the tail vein. The data are shown as mean±SEM. Results were analysed by ANOVA and different letters denote statistical significance (p<0.05).

Figure 3:
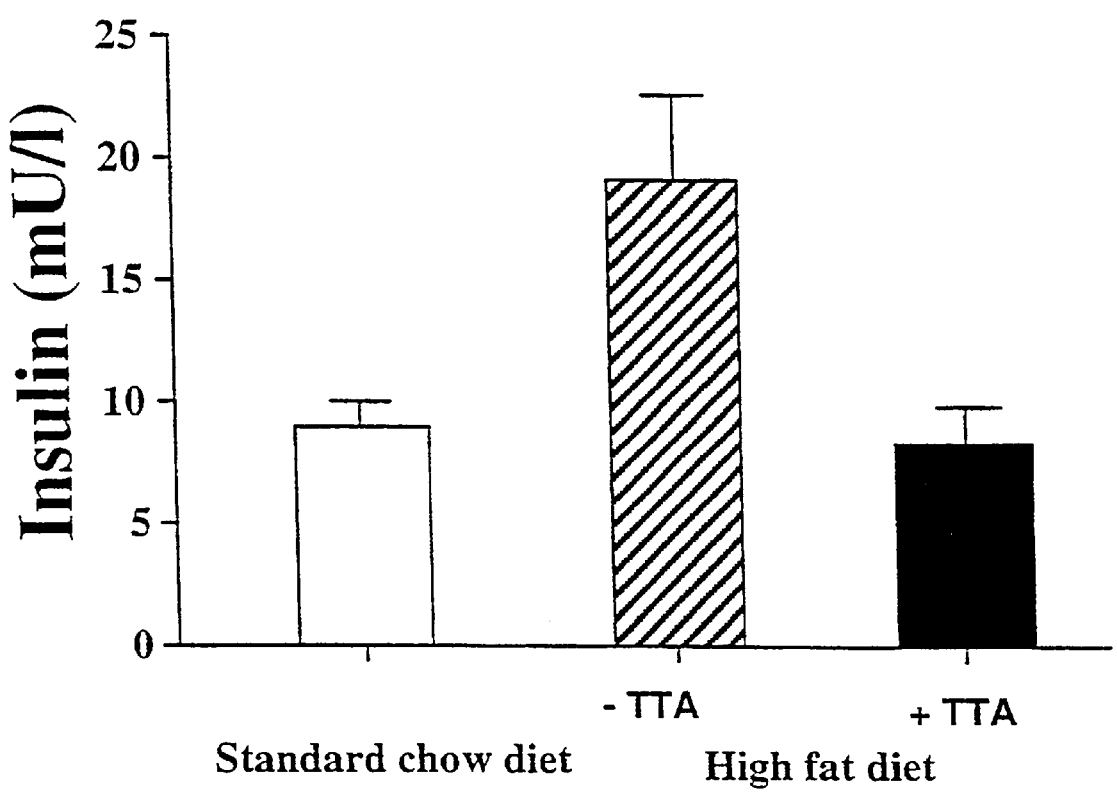
FIG. 3 shows that TTA treatment prevents high fat diet induced hyperinsulinemia.

FIG. 3 shows that the TTA treatment prevents high fat diet-induced hyperinsulinemia in Wistar Charles River rats.

EXAMPLE 12

TTA Treatment Prevents HF Diet Induced Insulin Resistance in Normal Rats

Rats weighing 330±20 g were divided into 3 groups (n=9) and fed with three different diets: standard rat chow, high fat diet (HF) and HF supplemented with TTA. After 21 days on their respective diets, a 90 min euglycemic hyperinsulinemic clamp was performed in unrestrained conscious animals as described under Materials and Methods. The glucose infusion rate (GIR) was determined from the period of the clamp where glycemia got stabilised, i.e. between 45–90 minutes after clamp commencement. The data are presented as mean±SEM.

An euglycemic hyperinsulinemic clamp protocol was set up to test whether dietary TTA intake would improve the high fat feeding-induced impairment of insulin action in the rat. The 90 min euglycemic hyperinsulinemic clamp resulted in plateau levels of plasma glucose and plasma insulin which were not different in the three groups studied. There was a significant reduction in the exogenous glucose infusion rate (GIR) required to maintain euglycemia in the HF group (FIG. 4) compared to the standard diet fed Wistar rats. Interestingly, the TTA supplementation of the HF diet prevented development of insulin resistance in these rats as evidenced by a fully normal GIR. This indicates a beneficial effect of TTA on insulin action in vivo.

Figure 4:
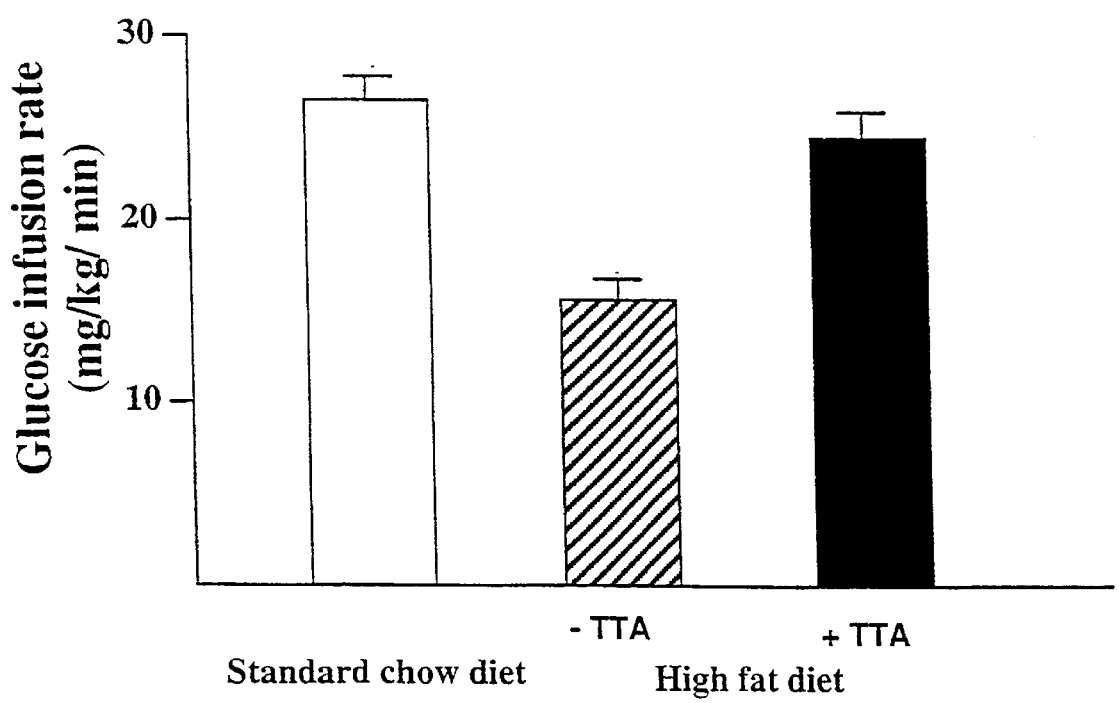
FIG. 4 shows that TTA treatment prevents high fat diet induced insulin resistance.

FIG. 4 shows that TTA treatment prevents high fat diet-induced insulin resistance in Wistar Charles River rats.

EXAMPLE 13

The Effect of TTA on the Plasma Levels of Insulin and Glucose in Obese Animals

5 Weeks Old Zucker (fa/fa) Rats

Figure 5:
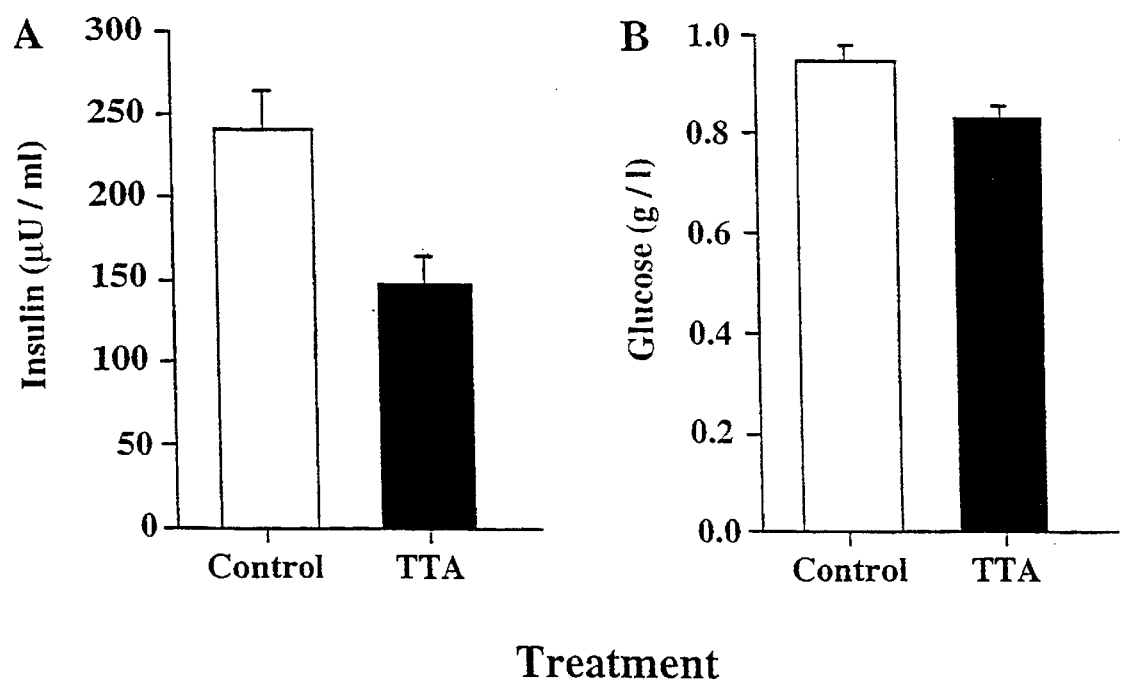
FIG. 5 shows that TTA treatment reduces blood insulin and glucose concentrations in 5 week old Zucker (fa/fa) rats.

As shown in FIG. 5, the TTA treatment reduced the blood insulin concentration by almost 40%, whereas the blood concentration of glucose was reduced approximately by 15%.

The rats were administered TTA at a dose of 300 mg/kg/day suspended in 0.5% CMC (n=6) by oral gavage. Following 11 days of treatment, rats were killed by cervical dislocation. Blood was collected and the levels of insulin and glucose measured as indicated in the method section. Data are means±S.D.

According to Zucker, L. M. et al. (Sparks, J. D. et al, Metabolism, 47, 1315–1324 1998.), these young animals have not developed hyperglycemia.

4 Month Old Obese Zucker (fa/fa) Rats

Figure 6:
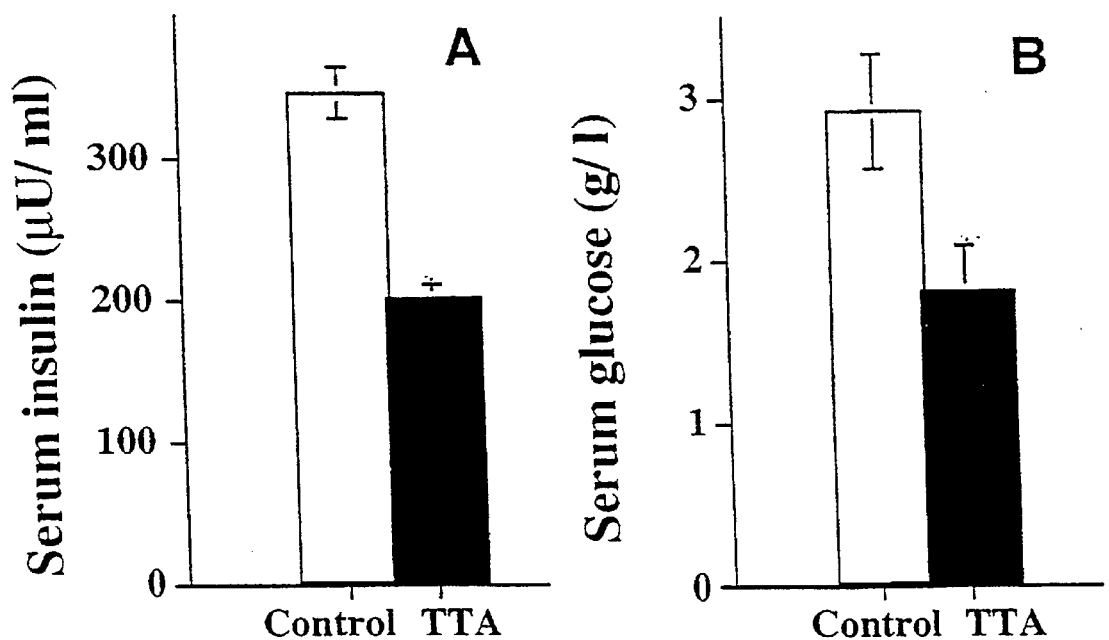
FIG. 6 shows that TTA treatment reduces blood insulin and glucose concentrations in 4 month old Zucker (fa/fa) rats (FIG. 5B.

FIG. 6 shows the effect on TTA on the levels of blood insulin and glucose in 4 month old Zucker (fa/fa) rats, i.e. rats which have developed hyperglycaemia (Sparks, J. D. et al, Metabolism, 47, 1315–1324 1998.),.

The rats were given a standard chow diet, either with (n=5) or without (n=6) 0.15% TTA. Following 21 days of treatment, blood was collected and the levels of insulin and glucose measured. Data are means±S.D.

EXAMPLE 15

TTA Treatment Decreases the Plasma Insulin Response to Glucose

Figure 7:
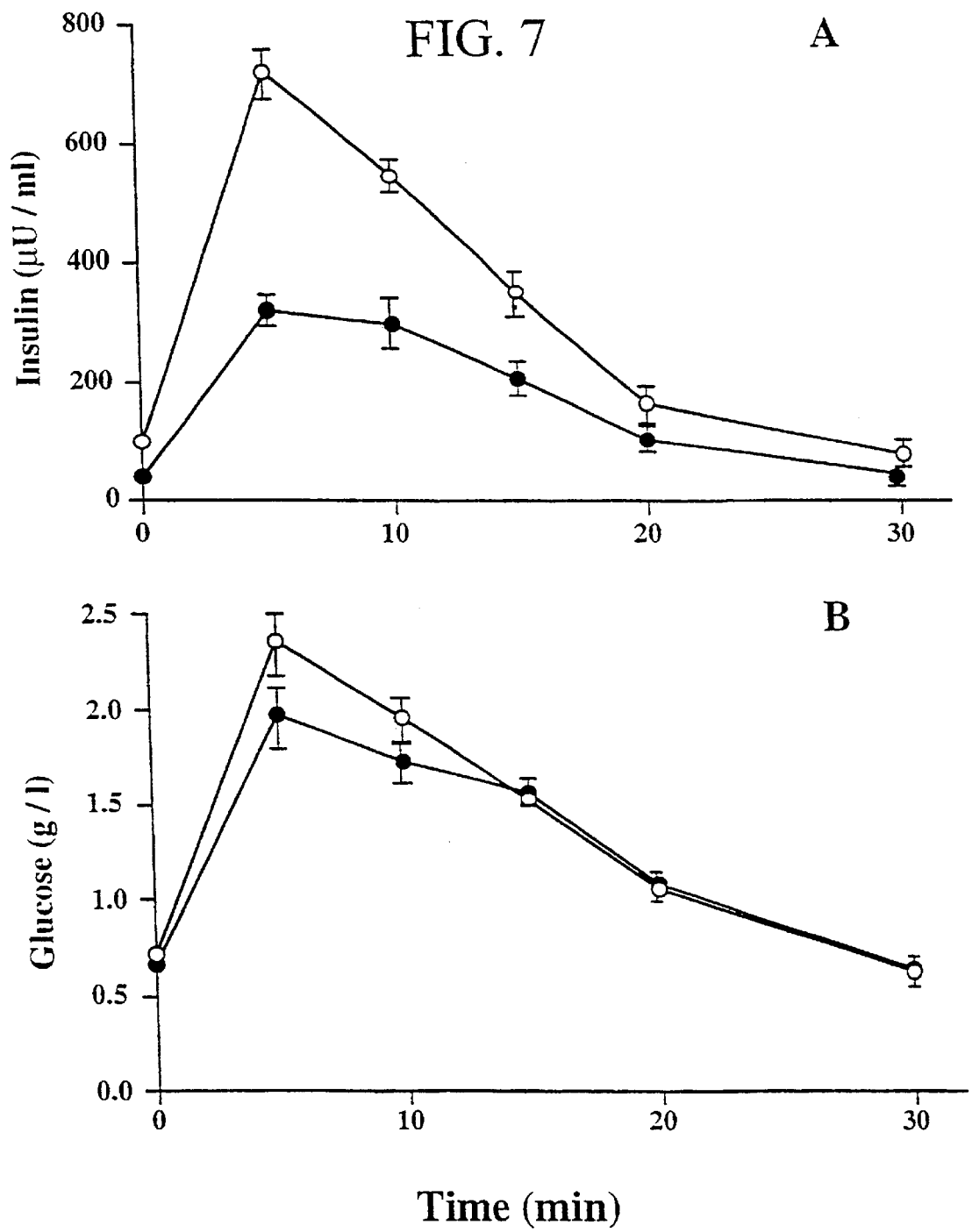
FIG. 7 shows that TTA treatment decreases the plasma insulin response to glucose.

To investigate whether TTA treatment resulted in an improvement of insulin action on glucose utilisation, an intravenous glucose tolerance test (IVGTT) were performed. In the 5 weeks old Zucker (fa/fa) rats, TTA treatment resulted in a significantly lower plasma insulin response to glucose (FIG. 7A). The IVGTT glucose curves were normal and comparable between TTA treated and control rats (FIG. 7B).

EXAMPLE 16

The Effect of TTA on Mitochondrial β-oxidation

Obese Zucker (fa/fa) rats were given a standard chow either with (n=6) or without (n=5) 0.15% TTA. Following 21 days of treatment, rats were killed by cervical dislocation and the livers were removed. Mitochondrial fractions were isolated from individual livers. Fatty acid oxidation rates were measured using [1-$^{14}$C]-palmitoyl CoA or [1-14C]-palmitoyl-L-carnitine as substrates (A) CPT-I (B) and CPT-II (C) were measured in the mitochondrial factions. RNA purification and hybridisation experiments were performed. The relative mRNA levels were determined by densiometric scanning of the autoradiograms and the different mRNA levels were normalised to the respective 28S rRNA and the means for the controls were set to 1. Formation of acid soluble products in control obese animals was 1.3±0.7 and 5.3±2.2 nmol/g liver/min using palmitoyl-CoA and palmitoyl-L-carnitine as substrates respectively. The CPT-I activity in control rats were 22.±4.9 nmol/g liver /min., and the CPT-II activity in control rats were 270±115 nmol/g liver/min. Values are expressed as the mean±S.D.

Figure 8:
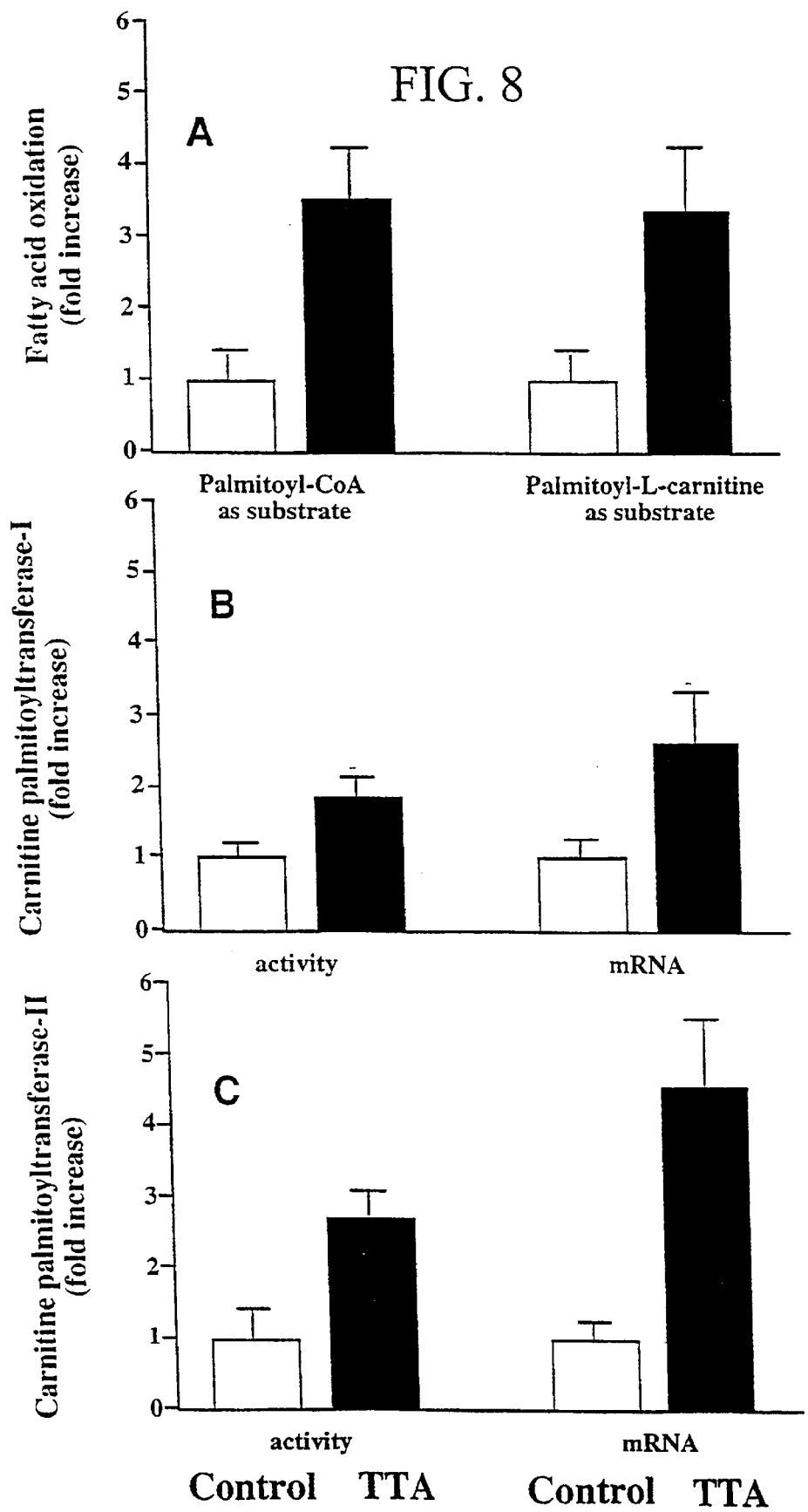
FIG. 8 shows that TTA increases the mitochondrial β-oxidation.

The TTA administration increased plasma concentrations of ketone bodies, resulting in a marked decrease in the FFA/ketone body ratio (Table 7). These data indicate that TTA treatment of 4 month old obese Zucker (fa/fa) rats increased hepatic mitochondrial β-oxidation and ketogenesis. Indeed, TTA treatment of obese Zucker (fa/fa) rats increased liver fatty acid oxidation more than 7-fold as measured with palmitoyl-CoA and palmitoyl-L-carnitine as substrates (FIG. 8A). This induction of b-oxidation was accompanied by an increase of activity and mRNA levels of both CPT-I (FIG. 8B) and CPT-II (FIG. 8C). Additionally, the activities of the rate-limiting enzymes in ketogenesis were increased (Table 7).

TABLE 7

Influence of TTA on plasma free fatty acids (FFA) and ketone bodies (4-hydroxy butyrate) concentration in old obese Zucker rats.

|  | FFA (mEq/L) | 4-OH butyrate (mmol/L) | FFA/ketone ratio | HMG-CoA synthase activity (nmol/min/mg protein) |
|---|---|---|---|---|
| Control | 0.76 ± 0.13 | 1.97 ± 0.33 | 0.40 ± 0.10 | 13 ± 4 |
| TTA | 0.53 ± 0.21 | 3.44 ± 1.37 | 0.17 ± 0.09 | 27 ± 6 |

Data are means±SD of six animals in both the control- and the experimental group. Free fatty acids (FFA) and ketone bodies (4-hydroxy butyrate) were measured in plasma and 3-hydroxy-3-methylglutaryl (HMG)—CoA synthase activities were measured in mitochondrial fractions prepared from the liver from 21 week-old male obese Zucker (fa/fa) rats given either a standard diet (control) or a standard diet enriched with 0.15% TTA for 15 days.

EXAMPLE 17

The Effect of TTA on Hepatic Levels of Triacylglycerol

The significant increased mitochondrial fatty acid oxidation caused by TTA will reduce the availability of fatty acids for esterification. The synthesis of triacylglycerol and cholesterol is thus reduced, and the secretion of VLDL from the liver is decreased. This is reflected in a decreased level of triacylglycerol in the liver, reduced plasma triacylglycerol, and reduced adipose tissue mass. Basal and total lypolysis are not changed (data not shown) and the ratio between plasma free fatty acids and ketone bodies is decreased (data not shown). This indicates an increased flux of fatty acids from the peripheral tissues to the liver for oxidation.

Even an increased hepatic level of triacylglycerol may be relieved by TTA. Feeding rats with an inhibitor of fatty acid oxidation will increase the level of hepatic triacylglycerol resulting in fatty liver. Tetradecyl-4-thia propionic acid (TTP) is a fatty acid analogue with a sulphur atom in the 4 position. This analogue inhibits the β-oxidation of fatty acids due to the formation of a mitochondrial inhibitor. Feeding rats with this analogue results in the formation of fatty. However, if the rats are fed with a combination of TTA and TTP, the formation of fatty liver is avoided (Table 8). This provides evidence that TTA may be used for the treatment of conditions with an increased hepatic level of triacylglycerol.

Male Wistar rats had free access to water and rat maintenance chow. They were fed palmitic acid or fatty acid analogues suspended in 0.5% CMC for 6 days. In some experiments TTA or TTP were fed for 3 days before feeding both for 6 days. At the end of the experiment the rats were fasted overnight, killed, the liver removed and homogenized. Triacylglycerol was measured in the homogenate.

TABLE 8

Hepatic levels of triacylglycerol in rats treated with palmitic acid and fatty acid analogues for 6 days. (TTA: 150 mg/kg/day - TTP: 300 mg/kg/day).

| 3 days prefeed. | | | | TTA | TTP |
|---|---|---|---|---|---|
| 6 days | Palm | TTA | TTP | TTA + TTP | TTP + TTA |
| TG (μmol/g) | 10.9 ± 3.3 | 7.7 ± 2.9 | 95.4 ± 14.7 | 15.1 ± 1.7 | 33.1 ± 7.6 |

EXAMPLE 18

Fatty acid analogues have been synthesised where the sulphur atom is moved to positions further from the carboxylic group of the fatty acid. When the sulphur atom is placed in positions on the carbon chain with odd numbers (5,7,9 etc.), these analogues will be partially β-oxidised. β-oxidation removes two C atoms at a time from the carboxylic end of the fatty acid, and such analogues may thus be β-oxidised until the sulphur atom is in the 3-position. It is thus conceivable that such analogues may have biological effects similar to TTA. Experiments have shown that fatty acid analogues related by having a sulphur atom in an odd numbered position on the carbon chain will all increase the mitochondrial β-oxidation (Table 9).

The mitochondrial β-oxidation is measured as in example 16 with the use of [1-$^{14}$C]-palmitoyl-L-carnitine as substrates.

TABLE 9

Effect of different fatty acid analogues on mitochondrial β-oxidation in rat liver.

| Position of S atom | 3 | 5 | 7 | Control: Palmitidic acid |
|---|---|---|---|---|
| Activity (nmol/min/ mg protein) | 0.81 ± 0.16 | 0.61 ± 0.06 | 0.58 ± 0.09 | 0.47 ± 0.06 |

EXAMPLE 19

Male obese Zucker fa/fa rats, weighing 100 g at the start of the experiment, were housed in pairs in metal wire cages in a room maintained at 12 h light-dark cycles and a constant temperature of 20±° C. The animals were acclimatised for at least one week under these conditions before the start of the experiment.

TTA and palmitic acid (control), was suspended in 0.5% (w/v) carboxymethyl cellulose (CMC) and administered at a dose of 300 mg/day/kg body weight, by gastric intubation (gavage) once daily for 10 days. The rats were fasted for 2 hours before termination of the experiment. Blood and organs were collected. Total lipids were extracted from liver and plasma. The lipids were evaporated, saponified and esterified prior to separation using a Carlo Erba 2900 gas-chromatograph.

TABLE 10

Effect of Compound I (tetradecylthioacetic acid) on fatty acid composition in obese Zucker fa/fa rats.

| | Oleic acid | Monounsaturated tetradecylthioacetic acid |
|---|---|---|
| Fatty acid composition in liver (% of total) | | |
| Control | 9.9 ± 1.4 | 0.0 |
| Compound I | 14.9 ± 1.0 | 1.1 ± 0.2 |
| Fatty acid composition in plasma (% of total) | | |
| Control | 18.3 ± 0.9 | 0.0 |
| Compound I | 22.1 ± 0.5 | 0.2 ± 0.1 |

Table 10 shows that oral administration of TTA increases the level of oleic acid in both liver and plasma. Also a delta-9-desaturated product of TTA accumulated in both plasma and liver.

What is claimed is:

1. A method for the treatment or prevention of an obese or overweight condition, comprising administering to an animal in need thereof a therapeutically effective amount of at least one fatty acid analogue of the general formula (I)

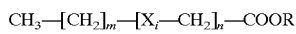

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ alkyl, with the proviso that at least one of the $X_i$ is not $CH_2$, or a salt, prodrug, or complex thereof.

2. The method of claim 1, wherein the animal is a human.
3. The method of claim 1, wherein the animal is an agricultural animal.
4. The method of claim 1, wherein the animal is a domestic animal.
5. The method of claim 1, wherein the animal is a fish or shellfish.
6. The method of claim 1, wherein m is greater than or equal to 13.
7. The method of claim 1, wherein $X_{i=3}$ is selected from the group consisting of O, S, SO, $SO_2$, and Se, and wherein $X_{i=5\text{-}25}$ is $CH_2$.
8. The method of claim 7, wherein $X_{i=3}$ is S.
9. The method of claim 7, wherein $X_{i=3}$ is Se.
10. The method of claim 1, wherein the fatty acid analogue is administered such that its concentration is maintained substantially continuously in the blood of the animal for the duration of the period of administration.
11. The method of claim 1, wherein the composition is in unit dosage form.
12. A method for producing weight loss or a reduction of the fat mass in a human or non-human animal comprising administering a therapeutically effective amount of a composition comprising at least one fatty acid analogue of the general formula (I)

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ alkyl, with the proviso that at least one of the $X_i$ is not $CH_2$, or a salt, prodrug, or complex thereof.

13. The method of claim 12, wherein the animal has developed an obese condition.
14. The method of claim 12, wherein the animal is low energy adapted.
15. The method of claim 12, wherein m is greater than or equal to 13.
16. The method of claim 12, wherein $X_{i=3}$ is selected from the group consisting of O, S, SO, $SO_2$, and Se, and wherein $X_{i=5\text{-}25}$ is $CH_2$.
17. The method of claim 16, wherein $X_{i=3}$ is S.
18. The method of claim 16, wherein $X_{i=3}$ is Se.
19. The method of claim 12, wherein the fatty acid analogue is administered such that its concentration is maintained substantially continuously in the blood of the animal for the duration of the period of administration.
20. The method of claim 12, wherein the composition is in unit dosage form.
21. The method of claim 12, wherein the animal is a human.
22. A method for the modification of the fat distribution and content of an animal, comprising administering to the animal food or a feed product comprising at least one fatty acid analogue of the general formula (I)

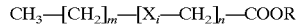

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ alkyl, with the proviso that at least one of the $X_i$ is not $CH_2$, or a salt, prodrug, or complex thereof.

23. The method of claim 22, wherein the animal is a human.
24. The method of claim 22, wherein the animal is an agricultural animal.
25. The method of claim 22, wherein the animal is a domestic animal.
26. The method of claim 22, wherein the animal is a fish or shellfish.
27. The method of claim 22, wherein m is greater than or equal to 13.
28. The method of claim 22, wherein $X_{i=3}$ is selected from the group consisting of O, S, SO, $SO_2$, and Se, and wherein $X_{i=5\text{-}25}$ is $CH_2$.
29. The method of claim 28, wherein $X_{i=3}$ is S.

30. The method of claim 28, wherein $X_{i=3}$ is Se.

31. The method of claim 22, wherein the fatty acid analogue is administered such that its concentration is maintained substantially continuously in the blood of the animal for the duration of the period of administration.

32. The method of claim 22, wherein the composition is in unit dosage form.

33. A method for the treatment or prevention of hypertension, comprising administering to an animal in need thereof a therapeutically effective amount of at least one fatty acid analogue of the general formula (I)

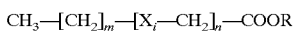

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ alkyl, with the proviso that at least one of the $X_i$ is not $CH_2$, or a salt, prodrug, or complex thereof.

34. The method of claim 33, wherein the animal is a human.

35. The method of claim 33, wherein the animal is an agricultural animal.

36. The method of claim 33, wherein the animal is a domestic animal.

37. The method of claim 33, wherein the animal is a fish or shellfish.

38. The method of claim 33, wherein m is greater than or equal to 13.

39. The method of claim 33, wherein $X_{i=3}$ is selected from the group consisting of O, S, SO, $SO_2$, and Se, and wherein $X_{i=5-25}$ is $CH_2$.

40. The method of claim 39, wherein $X_{i=3}$ is S.

41. The method of claim 39, wherein $X_{i=3}$ is Se.

42. The method of claim 39, wherein the fatty acid analogue is administered such that its concentration is maintained substantially continuously in the blood of the animal for the duration of the period of administration.

43. The method of claim 39, wherein the composition is in unit dosage form.

44. A method for the treatment or prevention of fatty hepatosis, comprising administering to an animal in need thereof a therapeutically effective amount of at least one fatty acid analogue of the general formula (I)

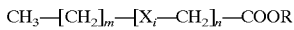

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ alkyl, with the proviso that at least one of the $X_i$ is not $CH_2$, or a salt, prodrug, or complex thereof.

45. The method of claim 44, wherein the animal is a human.

46. The method of claim 44, wherein the animal is an agricultural animal.

47. The method of claim 44, wherein the animal is a domestic animal.

48. The method of claim 44, wherein the animal is a fish or shellfish.

49. The method of claim 44, wherein m is greater than or equal to 13.

50. The method of claim 44, wherein $X_{i=3}$ is selected from the group consisting of O, S, SO, $SO_2$, and Se, and wherein $X_{i=5-25}$ is $CH_2$.

51. The method of claim 50, wherein $X_{i=3}$ is S.

52. The method of claim 50, wherein $X_{i=3}$ is Se.

53. The method of claim 44, wherein the fatty acid analogue is administered such that its concentration is maintained substantially continuously in the blood of the animal for the duration of the period of administration.

54. The method of claim 44, wherein the composition is in unit dosage form.

55. A method for the treatment or prevention of a metabolic syndrome characterized by hyperinsulinemia, insulin resistance, obesity, glucose intolerance, Type 2 diabetes mellitus, dyslipdemia and hypertension, comprising administering to an animal in need thereof a therapeutically effective amount of at least one fatty acid analogue of the general formula (I)

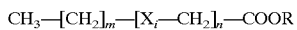

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ aklyl, with the proviso that at least one of the $X_i$ is not $CH_2$, or a salt, prodrug, or complex thereof.

56. The method of claim 55, wherein the animal is a human.

57. The method of claim 55, wherein the animal is an agricultural animal.

58. The method of claim 55, wherein the animal is a domestic animal.

59. The method of claim 55, wherein the animal is a fish or shellfish.

60. The method of claim 55, wherein m is greater than or equal to 13.

61. The method of claim 55, wherein $X_{i=3}$ is selected from the group consisting of O, S, SO, $SO_2$, and Se, and wherein $X_{i=5-25}$ is $CH_2$.

62. The method of claim 61, wherein $X_{i=3}$ is S.

63. The method of claim 61, wherein $X_{i=3}$ is Se.

64. The method of claim 55, wherein the fatty acid analogue is administered such that its concentration is maintained substantially continuously in the blood of the animal for the duration of the period of administration.

65. The method of claim 55, wherein the composition is in unit dosage form.

66. A fatty acid analogue of the general formula (I)

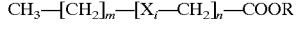

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ alkyl, with the proviso that at least one of the $X_i$ is not $CH_2$, and that if there is only 1 $X_i$ that is not —$CH_2$—, then $X_{i=3}$ is $CH_2$, or a salt, prodrug, or complex thereof.

67. A pharmaceutical composition for the prevention and treatment of obesity in animals comprising a fatty acid analogue of the general formula (I)

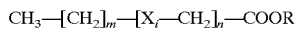

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ aklyl, with the proviso that at least one of the $X_i$ is not $CH_2$, and that if there is only 1 $X_i$ that is not —$CH_2$—, then $X_{i=3}$ is $CH_2$, or a salt, prodrug, or complex thereof, and a pharmaceutically acceptable carrier or excipient.

68. A nutritional composition comprising an amount of fatty acid analogue of the general formula (I)

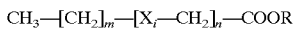

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ alkyl, or a salt, prodrug, or complex thereof, with the proviso that at least one of the $X_i$ is not $CH_2$, and that if there is only 1 $X_i$ that is not —$CH_2$—, then $X_{i=3}$ is $CH_2$, and the amount of the fatty acid analogue is effective to reduce or maintain the total body weight or total body fat mass in an animal.

* * * * *